(12) United States Patent
Greenwood et al.

(10) Patent No.: US 9,032,636 B2
(45) Date of Patent: May 19, 2015

(54) SYSTEM AND METHOD FOR INSPECTION OF SOFT GOODS

(75) Inventors: Kyle L. Greenwood, Bryan, TX (US); Chad Ottaberry, Bryan, TX (US)

(73) Assignee: Black Mountain Industries, Inc., Bryan, TX (US)

( * ) Notice: Subject to any disclaimer, the term of this patent is extended or adjusted under 35 U.S.C. 154(b) by 556 days.

(21) Appl. No.: 13/474,667

(22) Filed: May 17, 2012

(65) Prior Publication Data

US 2013/0305847 A1 Nov. 21, 2013

(51) Int. Cl.
*G01B 3/14* (2006.01)
*G01N 33/36* (2006.01)

(52) U.S. Cl.
CPC ................................. *G01N 33/367* (2013.01)

(58) Field of Classification Search
None
See application file for complete search history.

(56) References Cited

U.S. PATENT DOCUMENTS 2,713,210 A * 7/1955 Lobachewski ................ 33/563
2009/0025245 A1 * 1/2009 Brady ............................ 33/562

* cited by examiner

*Primary Examiner* — Robert R Raevis
(74) *Attorney, Agent, or Firm* — Tumey L.L.P.

(57) ABSTRACT

A system and method for inspection and quality control for goods determines whether the goods comply with desired configurations. In an embodiment, an inspection and quality control system for a good includes a template. The template includes a template body and a positive offset. The positive offset includes a maximum length of the good and a maximum width of the good. The positive offset is configured for the good to be disposed in the positive offset when the good is less than the maximum length and the maximum width. The system also includes a negative inset. The negative inset includes a minimum length for the good and a minimum width for the good. The negative inset is configured to be disposed in the positive offset over the good disposed in the positive offset.

20 Claims, 2 Drawing Sheets

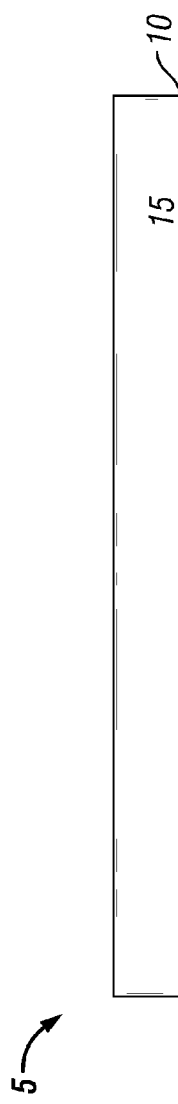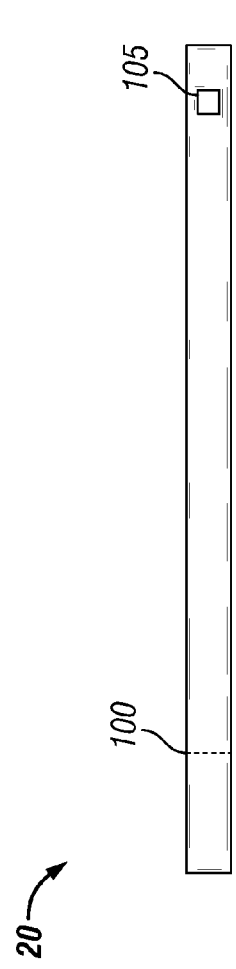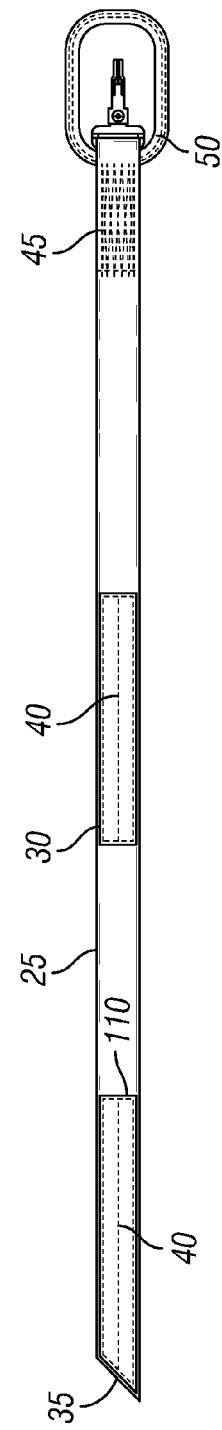

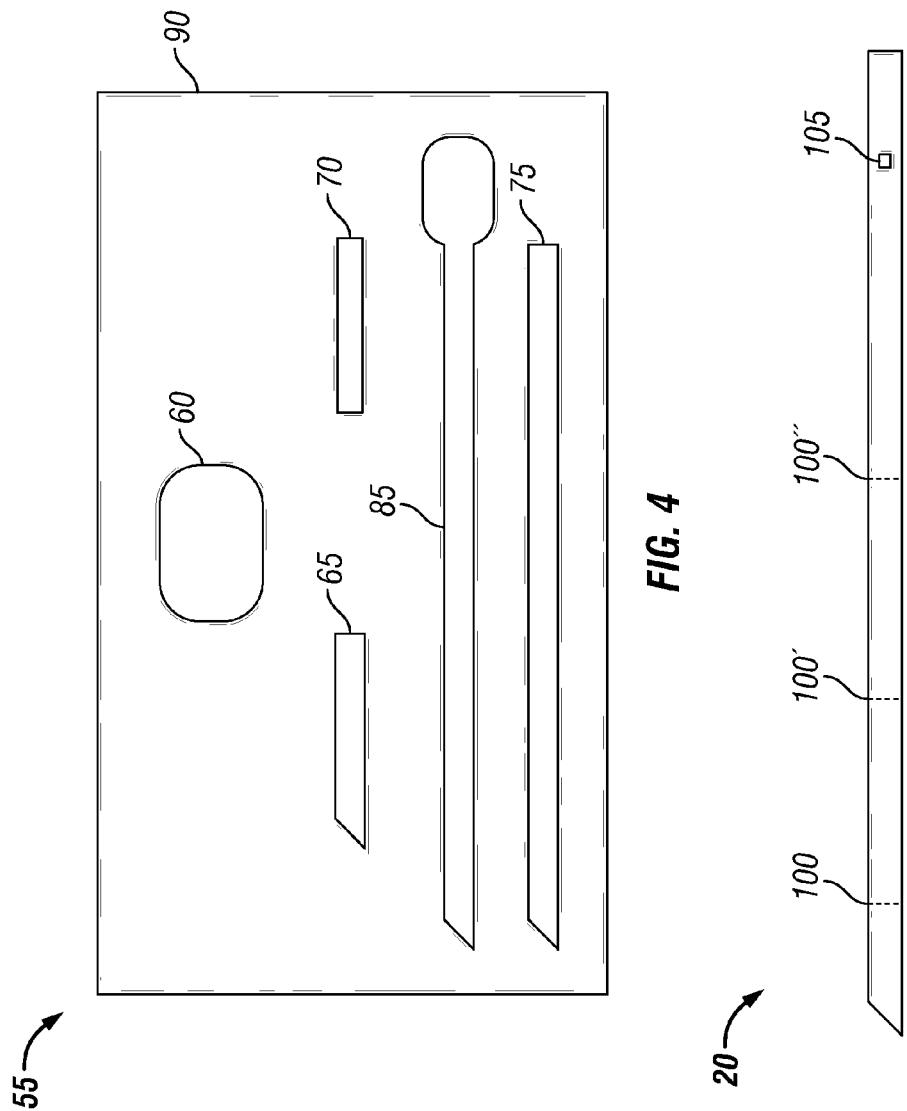

SYSTEM AND METHOD FOR INSPECTION OF SOFT GOODS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

This invention relates to the field of manufacturing and more specifically to the field of inspection and quality control methods and systems for soft goods using positive offsets and negative insets.

2. Background of the Invention

There are increased needs for improving the efficiency of manufacturing goods such as soft goods. Improving efficiency includes decreasing the time to finish production of quality products so that such products may be provided to the customer. Methods for improving such efficiency include improved methods for quality control and inspection of goods before being approved. A variety of methods are used for such quality control and inspection. Such methods include the use of calibrated measurement devices to measure each good and parts of each good. Such measurements are typically made to ensure that the goods satisfy tolerances for sizes and shapes. Drawbacks to such conventional methods include reductions in efficiencies in approving goods for the tolerances. For instance, inspectors typically inspect each good and often each part of each good to approve each good.

Consequently, there is a need for improved systems and methods for quality control and inspection of goods.

BRIEF SUMMARY OF SOME OF THE PREFERRED EMBODIMENTS

These and other needs in the art are addressed in one embodiment by an inspection and quality control system for a good that includes a template. The template includes a template body and a positive offset. The positive offset includes a maximum length of the good and a maximum width of the good. The positive offset is configured for the good to be disposed in the positive offset when the good is less than the maximum length and the maximum width. The system also includes a negative inset. The negative inset includes a minimum length for the good and a minimum width for the good. The negative inset is configured to be disposed in the positive offset over the good disposed in the positive offset.

These and other needs in the art are also addressed by a method for inspection and quality control of a good. The method includes determining whether the good is disposable in a positive offset or not disposable in the positive offset. The positive offset is disposed in a template. The method also includes placing a negative inset in the positive offset over the good when the good is disposable in the positive offset. The negative inset comprises a minimum length for the good and a minimum width for the good. In addition, the method includes determining whether the good comprises a length about the same or greater than the minimum length for the good and whether the good comprises a width about the same or greater than the minimum width for the good. The method also includes approving the good when the good is disposable in the positive offset and comprises a length about the same or greater than the minimum length for the good and a width about the same or greater than the minimum width for the good.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which:

FIG. 1 illustrates an embodiment of a template with a positive offset;

FIG. 2 illustrates an embodiment of a negative inset;

FIG. 3 illustrates an embodiment of a restraint belt;

FIG. 4 illustrates an embodiment of a template system; and

FIG. 5 illustrates an embodiment of a negative insert for a restraint belt.

DETAILED DESCRIPTION OF THE PREFERRED EMBODIMENTS

In an embodiment, an inspection and quality control system for goods includes a positive offset and a negative inset. In embodiments, the positive offset is configured for a particular good. The good may be disposed in the positive offset, and the negative inset may be placed over the good. Without limitation, the inspection and quality control system provides reliability for inspecting and controlling product quality. For instance, the positive offset and negative inset allow an inspector to ensure that each good is within a desired maximum size (i.e, by the positive offset) and within a desired minimum size (i.e., by the negative inset). Further, without limitation, the inspection and quality control system provides improved efficiency for inspection and quality control by providing the positive offset and negative inset, which may be used repeatedly for the particular good. In addition, without limitation, the inspection and quality control system provides improved speed for the inspection and quality control. For instance, an inspector may not inspect (i.e., measure and the like) each produced good, but instead may select a certain number of random samples of the good to approve by the inspection and quality control system. In some embodiments, an inspector may approve the positive offset and negative inset instead of inspecting goods themselves. In an embodiment, the inspection and quality control system approves the length and width of goods in the assembled and sub-assembled stages.

The inspection and quality control system may be used for any desired goods. In an embodiment, the goods are soft goods. Soft goods include any goods that include pliable material such as pliable fabric. In some embodiments, the soft goods may be twisted and/or stretched. Without limitation, examples of soft goods include foam, fabric, webbing, cloth, and the like.

In an embodiment, the inspection and quality control system include a template 5 as shown in FIG. 1. Template 5 includes template body 10 and positive offset 15. Template body 10 includes any material suitable for use in inspection and quality control of goods. In an embodiment, template body 10 comprises substantially rigid material. Without limitation, examples of suitable materials include wood, metal, plastic, and the like. In embodiments, template body 10 comprises polyvinyl chloride (e.g., PVC).

As shown in FIG. 1, embodiments of the inspection and quality control system include positive offset 15 disposed in template body 10. Positive offset 15 is a removed portion of template body 10 in the configuration and shape of a desired good or part of a good (e.g., sub-assembly part). The positive offset 15 has sufficient dimensions to allow the good and a corresponding negative inset to be placed in the positive offset 15 when of approved dimensions. In embodiments, positive offset 15 is configured to provide a maximum desired length and width of a good or sub-assembly good. For instance, when a good fits within positive offset 15 when placed in positive offset 15, the good is less than the desired maximum size (e.g., length and width) of the good. In an embodiment, positive offset 15 is configured for a tolerance. In such an embodiment, the length and width of positive offset 15 is at the maximum of the positive tolerance for the good. As an example, a good to be approved is desired to have a length of x with a tolerance of ±y and a width of a with a tolerance of ±b. In such an example, positive offset 15 is configured to have a length of x+y and a width of a+b.

As shown in FIG. 2, embodiments of the inspection and quality control system include negative inset 20. Negative inset 20 is in the configuration and shape of a desired good or part of a good (e.g., sub-assembly good). It is to be understood that sub-assembly goods refer to goods that when assembled together are an assembled good. In embodiments, negative inset 20 corresponds in configuration to a positive offset 15 for the good. The negative inset 20 has a smaller width and length than the corresponding positive offset 15, which allows negative inset 20 to be placed in positive offset 15. In embodiments, negative inset 20 is configured to provide a minimum desired length and width of a good. For instance, when a good fits within positive offset 15 when placed in positive offset 15, negative inset 20 is placed in positive offset 15 over the good. If the good has a length and width larger than negative inset 20 or about the same as negative inset 20, the good has at least the minimum desired length and width. In an embodiment, negative inset 20 is configured for a tolerance. In such an embodiment, the length and width of negative inset 20 is at the minimum of the negative tolerance for the good. As an example, a good to be approved is desired to have a length of x with a tolerance of ±y and a width of a with a tolerance of ±b. In such an example, negative inset 20 is configured to have a length of x−y and a width of a−b.

Negative inset 20 may be composed of any material suitable for use in inspection and quality control of goods. In an embodiment, negative inset 20 comprises substantially rigid material. Without limitation, examples of suitable materials include wood, metal, plastic, and the like. In embodiments, negative inset 20 comprises polycarbonate. In some embodiments, negative inset 20 is transparent or semi-transparent. In an embodiment, negative inset 20 is transparent. Without limitation, negative inset 20 is transparent or semi-transparent to allow an inspector to visually determine if a good has a minimum desired length and width and/or is within the minimum desired tolerance for length and width.

In embodiments as further shown in FIG. 2, negative inset 20 has one or more length check means 100. Length check means 100 include any means disposed on negative inset 20 suitable for identifying the desired longitudinal location of an object disposed on negative inset 20. In an embodiment, length check means 100 is disposed at a location on negative inset 20 that indicates the location of a desired end of an object on negative inset 20. For instance, a stitching on negative inset 20 may be desired to have an end point at a certain location on negative inset 20. In such an instance, length check means 100 are disposed at such certain location and if the end point is about at length check means 100, such disposition indicates that the object's end point is at the desired location. It is to be understood that negative inset 20 is not limited to one length check means 100 but may have more than one length check means 100. In an embodiment, length check means 100 is used to determine that an object has a desired length. In such an embodiment, negative inset 20 has two length check means 100 with the length check means 100 separated by a desired distance that indicates the desired length of the object. When each end of the object is disposed at about a length check means 100, such dispositions indicate that the object has the desired length. Length check means 100 may include any desirable means for indicating the disposition of an object. Without limitation, examples of suitable length check means 100 include marks, dashes, a window (e.g., an opening through negative inset 20), and the like on negative inset 20. In an embodiment, the length check means 100 are marks on negative inset 20. For instance, as shown in the embodiment of FIG. 2, length check means 100 are a series of dashes that extend about laterally on negative inset 20. In an embodiment in which negative inset 20 is transparent or semi-transparent, the location of a desired object in relation to the dashes is visible through the negative insert 20.

As further shown in FIG. 2, negative inset 20 has window 105. Window 105 is a removed section of negative inset 20. In some embodiments, the removed section extends laterally through negative inset 20. Window 105 may be disposed on negative inset 20 at any position in which it is desired to confirm position of an object on a good (i.e., when the object is visible within window 105). In embodiments, the size of window 105 may also take into account any tolerances for the object (i.e., if the object is within window 105, then it is within the desired tolerance).

In an embodiment, positive offset 15 has a depth sufficient for the good and negative inset 20 to both be placed therein.

In an embodiment as shown in FIG. 4, the inspection and quality control system includes template system 55. In such an embodiment, template system 55 includes a plurality of positive offsets and negative insets. Without limitation, the inspection and quality control system allows for inspection and quality control of a product at the sub-assembly level and also at the assembled good level. For instance, in an embodiment in which the assembled good includes various parts that are separate from each other before being assembled into the final assembled good (e.g., that are separate at the sub-assembly level), the inspection and quality control system may have positive offsets and negative insets for each sub-assembled good and also for the assembled good. Without limitation, by providing the inspection and quality control at the sub-assembly level, non-conforming parts are identified before the assembly level, which prevents rejection of the assembled good because of the non-conforming part. Such non-conforming part may not then be assembled into the final assembled good (i.e., the product). Further, without limitation, such sub-assembly level inspection and quality control may provide significant cost and time savings.

FIG. 4 shows an embodiment in which the inspection and quality control of the sub-assembled parts and the assembled good of an embodiment of a restraint belt 25 as shown in FIG. 3 is carried out by the inspection and quality control system. It is to be understood that FIG. 4 shows an embodiment of the inspection and quality control system for a restraint belt 25 for illustration purposes only, and embodiments of the inspection and quality control system may be used for any desired sub-assembly and assembled goods. As shown in FIG. 3, restraint belt 25 comprises patch 30, end patch 35, and buckle pad 50, which are separate parts of restraint belt 25 during sub-assembly and are added to restraint belt 25 during its assembly. In the embodiment of template system 55 shown in FIG. 4, template system 55 includes buckle pad positive offset 60, end patch positive offset 65, patch positive offset 70, restraint belt positive offset 75, and assembled restraint belt positive offset 85. The template body is restraint belt template body 90. In the embodiment as shown, restraint belt template body 90 contains the positive offsets for the sub-assembled parts (e.g., buckle pad positive offset 60, end patch positive offset 65, patch positive offset 70, and restraint belt positive offset 75) and the assembled restraint belt 25 product (e.g., assembled restraint belt positive offset 85). In alternative embodiments (not illustrated), template system 55 has more than one template body, in which one or more than one of the positive offsets may be disposed thereon.

As further shown in FIG. 4, each of the positive offsets for the sub-assembled parts has a corresponding negative inset. FIG. 5 illustrates an embodiment of a negative inset 20 for restraint belt positive offset 75. In such embodiment, negative inset 20 has length check means 100 and window 105. Length check means 100 indicates the desired location on restraint belt 25 of the end 110 of end patch 35. In an alternative embodiment (not illustrated), negative inset 20 may also have a window (not illustrated) disposed to indicate the desired lateral location of stitch line 40 on end patch 35. As further shown, embodiments of negative inset 20 include length check means 100' and 100", which are disposed with a length between that indicates the desired length of patch 30 as well as the desired locations of the longitudinal ends of patch 30. In an alternative embodiment (not illustrated), negative inset 20 may also have a window (not illustrated) disposed to indicate the desired lateral location of stitch line 40 on patch 30. Embodiments as shown also include negative inset 20 having window 105. In such embodiments, window 105 is disposed at a desired location in which the end of stitching 45 that is proximate to buckle pad 50 is disposed.

In an embodiment of a method for inspection and quality control of a product at the sub-assembly and assembly level, the sub-assembled goods (e.g., parts) are placed in the corresponding positive offsets. In embodiments in which the sub-assembled goods sufficiently fit within the corresponding positive offsets, the sub-assembled goods are within a maximum desired length and width (i.e., including any maximum tolerances). In embodiments in which any of the sub-assembled goods do not sufficiently fit within the corresponding positive offsets, the non-fitting sub-assembled goods may then be replaced or repaired before being assembled into the final assembled goods. In an embodiment in which the sub-assembled goods are within the maximum desired length and width (i.e., including any maximum tolerances), the method also includes placing the corresponding negative insets in the proper positive offsets over the sub-assembled good in the corresponding positive offset. In embodiments in which the sub-assembled goods are larger (e.g., length and width) or substantially the same size (e.g., length and width) as the corresponding negative insets, the sub-assembled goods are within a minimum desired length and width (i.e., including any minimum tolerances). In embodiments in which any of the sub-assembled goods are not larger or substantially the same size as the corresponding negative insets, the non-fitting sub-assembled goods may then be replaced or repaired before being assembled into the final assembled good. The method further includes checking any windows and length check means on the negative insets to confirm the desired length, presence, and the like of any objects (e.g., threads) on the sub-assembled good are satisfied. In embodiments in which any of the sub-assembled goods do not satisfy the desired length, presence and the like of the windows and length check means, the non-conforming sub-assembled goods may then be replaced or repaired before being assembled into the final assembled good. In embodiments in which the sub-assembled goods are larger or substantially the same size as the negative insets and are also confirmed to satisfy any windows and length check means, the sub-assembled goods may then be assembled into the final product.

In embodiments, the method includes assembling the conforming sub-assembled goods into the assembled final good. In an embodiment, the assembled final good (i.e., the assembled product) may then be placed in the corresponding positive offset. In embodiments in which the assembled good sufficiently fits within the corresponding positive offset, the assembled good is within a maximum desired length and width (i.e., including a maximum tolerance). In embodiments in which the assembled good does not sufficiently fit within the corresponding positive offset, the non-fitting assembled good may then be replaced or repaired. In embodiments in which the assembled good is within a maximum desired length and width (i.e., including a maximum tolerance), the method further includes placing the corresponding negative inset in the positive offset (e.g., corresponding to the assembled good) over the assembled good in the positive offset. In embodiments in which the assembled good is larger or substantially the same as the corresponding negative inset, the assembled good is within a minimum desired length and width (i.e., including a minimum tolerance). In embodiments in which the assembled good is not larger or substantially the same size as the negative inset, the non-conforming assembled good may then be replaced or repaired before being approved and sent to a destination such as a customer. The method further includes checking any windows and length check means on the negative inset to confirm the desired length, presence, and the like of any objects (e.g., patches and the like) on the assembled good are satisfied. In embodiments in which the method confirms that any of the objects do not satisfy the desired length, presence and the like of the windows and length checks, the non-conforming assembled good may then be replaced or repaired before being approved. In embodiments in which the assembled good is larger or substantially the same size as the negative inset and is also confirmed to satisfy any windows and length check means, the assembled good may then be approved.

Although the present invention and its advantages have been described in detail, it should be understood that various changes, substitutions and alterations may be made herein without departing from the spirit and scope of the invention as defined by the appended claims.

What is claimed is:

1. An inspection and quality control system for a good, comprising:
 a template, wherein the template comprises a template body and a positive offset, wherein the positive offset comprises a maximum length of the good and a maximum width of the good, and wherein the positive offset is configured for the good to be disposed in the positive offset when the good is less than the maximum length and the maximum width;

a negative inset, wherein the negative inset comprises a minimum length for the good and a minimum width for the good, and wherein the negative inset is configured to be disposed in the positive offset over the good disposed in the positive offset.

2. The inspection and quality control system of claim 1, wherein the good comprises a soft good.

3. The inspection and quality control system of claim 1, wherein the template comprises a substantially rigid material.

4. The inspection and quality control system of claim 1, wherein the maximum length and maximum width each comprise a positive tolerance.

5. The inspection and quality control system of claim 1, wherein the minimum length and the minimum width each comprise a negative tolerance.

6. The inspection and quality control system of claim 1, wherein the negative inset comprises a substantially rigid material.

7. The inspection and quality control system of claim 1, wherein the negative inset is transparent or semi-transparent.

8. The inspection and quality control system of claim 1, wherein the negative inset comprises a window.

9. The inspection and quality control system of claim 1, wherein the negative inset comprises a length check means.

10. The inspection and quality control system of claim 9, wherein the negative inset comprises at least two length check means, and wherein two of the length check means comprise a length between each other, and further wherein the length represents a length of an object on the good.

11. The inspection and quality control system of claim 1, wherein the good is an assembled good comprising an assembly of sub-assembled goods, and wherein the system further comprises a positive offset for at least one sub-assembled good and a negative inset for at least one sub-assembled good.

12. The inspection and quality control system of claim 11, wherein the positive offset for the at least one sub-assembled good comprises a maximum length for the at least one sub-assembled good and a maximum width for the at least one sub-assembled good.

13. The inspection and quality control system of claim 12, wherein the positive offset for the at least one sub-assembled good is configured for the sub-assembled good to be disposed in the positive offset for the at least one sub-assembled good when the sub-assembled good is less than the maximum length and the maximum width for the at least one sub-assembled good.

14. The inspection and quality control system of claim 11, wherein the negative inset for the at least one sub-assembled good comprises a minimum length for the at least one sub-assembled good and a minimum width for the at least one sub-assembled good.

15. The inspection and quality control system of claim 14, wherein the negative inset for the at least one sub-assembled good is configured to be disposed in the positive offset for the at least one sub-assembled good and over the sub-assembled good disposed in the positive offset.

16. The inspection and quality control system of claim 15, wherein the sub-assembled good comprises a length and width about the same or greater than the minimum length and minimum width of the negative inset for the at least one sub-assembled good.

17. A method for inspection and quality control of a good comprises:
(A) determining whether the good is disposable in a positive offset or not disposable in the positive offset, wherein the positive offset is disposed in a template;
(B) placing a negative inset in the positive offset over the good when the good is disposable in the positive offset, wherein the negative inset comprises a minimum length for the good and a minimum width for the good;
(C) determining whether the good comprises a length about the same or greater than the minimum length for the good and whether the good comprises a width about the same or greater than the minimum width for the good; and
(D) approving the good when the good is disposable in the positive offset and comprises a length about the same or greater than the minimum length for the good and a width about the same or greater than the minimum width for the good.

18. The method of claim 17, wherein the good is an assembled good comprising an assembly of sub-assembled goods, and wherein the method further comprises determining whether at least one of the sub-assembled goods is disposable in a positive offset for sub-assembled goods.

19. The method of claim 18, wherein the positive offset for sub-assembled goods comprises a maximum length for the at least one of the sub-assembled goods and a maximum width for the at least one of the sub-assembled goods.

20. The method of claim 18, further comprising placing a negative inset for the at least one of the sub-assembled goods in the positive offset for the at least one sub-assembled goods over the at least one sub-assembled good, wherein the negative inset comprises a minimum length for the at least one sub-assembled good and a minimum width for the at least one sub-assembled good, and further comprises determining whether the at least one sub-assembled good comprises a length about the same or greater than the minimum length for the at least one sub-assembled good and whether the sub-assembled good comprises a width about the same or greater than the minimum width for the at least one sub-assembled good.

* * * * *